United States Patent
Wang et al.

(10) Patent No.: US 10,028,797 B2
(45) Date of Patent: Jul. 24, 2018

(54) ASEPTIC MEDICAL INSTRUMENT PACKAGING WITH SUPPORTING PEELABLE FLAPS

(71) Applicant: Qiang Wang, Hangzhou (CN)

(72) Inventors: Qiang Wang, Hangzhou (CN); Guohua Zhang, Hangzhou (CN)

( * ) Notice: Subject to any disclaimer, the term of this patent is extended or adjusted under 35 U.S.C. 154(b) by 0 days.

(21) Appl. No.: 15/255,947

(22) Filed: Sep. 2, 2016

(65) Prior Publication Data

US 2017/0065359 A1    Mar. 9, 2017

(30) Foreign Application Priority Data

Sep. 8, 2015    (CN) .......................... 2015 1 0566073
Sep. 8, 2015    (CN) ..................... 2015 2 0690357 U

(51) Int. Cl.
*A61B 50/30*    (2016.01)
*B65D 75/58*    (2006.01)
*A61B 50/00*    (2016.01)

(52) U.S. Cl.
CPC .......... *A61B 50/30* (2016.02); *B65D 75/5855* (2013.01); *A61B 2050/0065* (2016.02)

(58) Field of Classification Search
CPC ......... A61B 17/06; A61B 19/02; A61B 50/30; A61B 75/58; A61B 75/5855; A61B 2050/0065; B65D 33/00; B65D 33/007
USPC ............. 206/363–365, 438, 439, 484–484.2; 383/63–65, 94, 95
See application file for complete search history.

(56) References Cited

U.S. PATENT DOCUMENTS

| | | | | |
|---|---|---|---|---|
| 2,998,880 A | * | 9/1961 | Ladd ................. | B65D 75/5855 206/363 |
| 3,035,691 A | * | 5/1962 | Rasmussen ......... | A61M 25/002 206/364 |
| 3,419,137 A | * | 12/1968 | Walck, III .......... | B65D 75/5855 206/364 |
| 3,740,237 A | * | 6/1973 | Grindrod ........... | B65D 75/5855 383/211 |
| 3,926,311 A | * | 12/1975 | Laske .................... | A61B 50/30 206/439 |
| 3,995,739 A | * | 12/1976 | Tasch ..................... | A61B 50/30 206/439 |
| 7,073,666 B2 | * | 7/2006 | Arndt .................... | A61F 15/003 206/438 |
| 8,789,247 B2 | * | 7/2014 | Tanaka ............... | B65D 33/2508 383/63 |

(Continued)

*Primary Examiner* — Bryon Gehman
(74) *Attorney, Agent, or Firm* — Malloy & Malloy, P.L.

(57) ABSTRACT

An aseptic medical instrument packaging has supporting peelable flaps by adding a material playing a supporting role which is harder than the rest of an extending part outside a sealing edge of a peeling side of the packaging, or adopting a material which is harder than the rest of an extending part outside a sealing edge of the peeling side of the packaging. A groove is carved in a junction between an outer edge of a sealing edge of a peeling side of the packaging. The material playing the supporting role comprises hard plastic, metal and paper. A soft cover of the packaging is prevented from being curled inwardly in the process of peeling open the packaging; and when one or two peeling sides exist, the degree of differentiation the peeling side will be increased, such that medical staff can conveniently find the peeling side.

4 Claims, 2 Drawing Sheets

(56) References Cited

U.S. PATENT DOCUMENTS

2005/0031233 A1\* 2/2005 Varanese ................ B65D 33/20
                                                    383/211
2007/0104398 A1\* 5/2007 Ours ...................... B65D 33/18
                                                    383/211

\* cited by examiner

ASEPTIC MEDICAL INSTRUMENT PACKAGING WITH SUPPORTING PEELABLE FLAPS

TECHNICAL FIELD

The present invention belongs to the field of equipment packaging, in particular, to an aseptic medical instrument packaging with supporting peelable flaps.

BACKGROUND ART

Many clinically used articles need an aseptic packaging, for example, aseptic gloves, aseptic gauze, plaster, etc. The article 5.1.9c of the first part of Packaging for Terminally Sterilized medical instruments of ISO 11607-2006 which is applied at present prescribes that the peeling characteristics shall be continuous and homogenous, without delamination or tearing of the material that can affect aseptic opening and presentation. Article 7.3.5 of the Packaging for Terminally Sterilized Medical Instruments of GB/T 19633-2005 prescribes that in package-peeling, fiber falling and cracking or breaking off of the packaging material shall be in a specified limitation of a manufacturer to ensure no influence on the use of medical instruments. However, these standards, including pharmaceutical Industry Standards YY/T 0698, do not prescribe an inward curling degree of the peeling side of the packaging for the terminally sterilized medical instruments when peeled-open. At present, there are many types of medical aseptic packaging, for example, a pre-formed rigid tray is provided with a die-cut lid, flexible peel pouch, sterilization bag, header bag, form/fill/seal (FFS) and four-side-sealing (4SS) process, etc., (appendix A3 of the first part of ISO11607-2006), and one or both of the upper packaging surface and lower packaging surface of the packaging is usually soft. These aseptic packaging are provided with a peeling side/edge, i.e., an extending part (non-aseptic, a gripper part) outside the sealing edge that is wider than the other three sides. Of course, there are packaging with multiple peeling sides. In clinical practice, an operator peels the aseptic packaging, the operation standard requires that the peel-open flap is peeled while two faces (both soft) or one face (soft) of the packaging is turned outwardly and curled. In fact, when the peelable flap of the aseptic packaging is longer and cannot be grasped by the hands or the operator peels the package in a hasty manner, due to the influence of the non-peeled parts at two adjacent sides of the peelable flap, the part not grasped on the soft cover is turned inwardly and curled, and the germ-carrying extending part outside the sealing edge contacts with and contaminates contents, thereby increasing an infection risk. Further, damage from sealing fiber and scrap falling off of the packaging can lead to contamination of the contents. Therefore, there is a need for a controllable soft cover peeling direction of the packaging for aseptic medical instruments.

SUMMARY OF THE INVENTION

Aiming at the defects of the prior standards and prior art, the present invention provides "a controllable soft cover peeling direction of the packaging for aseptic medical instruments", the present invention also provides an aseptic medical instrument packaging with supporting peelable flaps.

The aseptic medical instrument packaging with supporting peelable flaps provides the supporting peelable flaps by adding a supporting material which is harder than the rest of an extending part of a supporting peelable flap outside a sealing edge of the peeling side of the packaging or adopting a material which is harder than the rest of the extending part of the supporting peelable flap outside a sealing edge of the peeling side of the packaging; the supporting material comprises hard plastic, metal and paper; the supporting peelable flap plays a supporting role like that of a flagpole when the packaging is peeled, to guide the soft cover of the packaging to be turned and curled toward a desired direction.

The hard plastic is phenolic plastic, polyurethane plastic, epoxy plastic, unsaturated polyester plastic, furan plastics, or plastic made of organic silicon resin, propenyl resin or modified resin.

The corners of the material playing a supporting role, which is harder than the rest of and added to the extending part outside a sealing edge of the peeling side of the packaging are passivated to avoid the damage of the packaging in a storage and transportation process.

The corners of the material playing a supporting role, which is harder than the rest of and adopted on the extending part outside a sealing edge of the peeling side of the packaging are passivated to avoid the damage of the packaging in a storage and transportation process.

The metal is aluminum, steel, iron, platinum or alloy.

A groove is carved in the junction between the outer edge of the sealing edge of the peeling side of the packaging and the extending part to facilitate peeling.

Beneficial effects: 1, the supporting peelable flap plays a supporting role like that of a flagpole when the packaging is peeled, and the soft cover of the packaging is prevented from being curled inwardly to contaminate the contents; 2, when there are only one or two peelable flaps, the degree of differentiation of the peeling side will be increased, such that medical staff can conveniently find the peeling side; 3, the present invention resolves the defects of the existing standards, and puts forwards the new concept of "a controllable soft cover peeling direction of the packaging for the aseptic medical instruments", and lays a foundation for our country to obtain certain rights to speak in the high end field of establishment of international standards of packaging for terminally sterilized medical instruments.

DETAILED DESCRIPTION OF THE INVENTION

Figure 1:
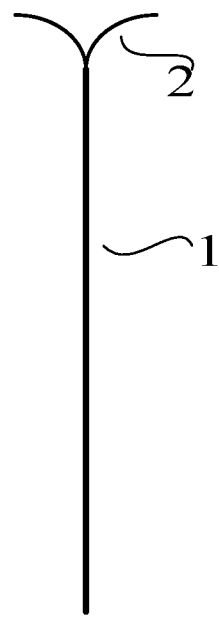
FIG. 1 is a side view of an extending part of the present invention which adopts hard plastic.
Figure 2:
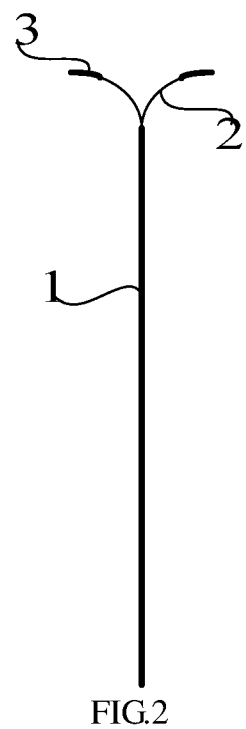
FIG. 2 is a side view of hard plastic strips added to an extending part of the present invention.
Figure 3:
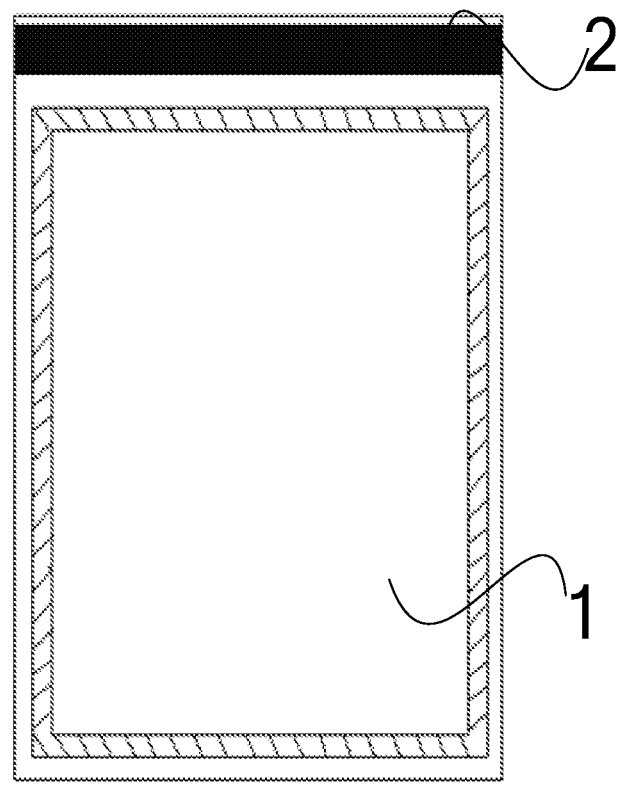
FIG. 3 is a front view of the present invention.

FIG. 1, FIG. 2 and FIG. 3, show an aseptic medical instrument packaging with supporting peelable flaps, the aseptic medical instrument packaging with supporting peelable flaps plays a supporting role by adding a material 3 which is harder than the rest of the extending part 2 outside a sealing edge of the peeling side of the packaging 1 or adopting a material which is harder than the rest of the extending part 2 outside a sealing edge of the peeling side of the packaging; the material playing the supporting role comprises hard plastic, metal and paper.

The hard plastic is phenolic plastic, polyurethane plastic, epoxy plastic, unsaturated polyester plastic, furan plastics, or plastic made of organic silicon resin, propenyl resin or modified resin.

The corners of the material playing a supporting role, which is harder than the rest of and added to the extending part outside a sealing edge of the peeling side of the packaging are passivated to avoid the damage of the packaging in a storage and transportation process.

The corners of the material playing a supporting role, which is harder than the rest of and adopted on the extending part outside a sealing edge of the peeling side of the packaging are passivated to avoid the damage of the packaging in a storage and transportation process.

The metal is aluminum, steel, iron, platinum or alloy.

A groove is carved in the junction between the outer edge of the sealing edge of the peeling side of the packaging and the extending part to facilitate peeling.

What is claimed is:

1. An aseptic medical instrument packaging with supporting peelable flaps, the supporting peelable flaps are formed by adding a supporting material which is harder than an extending part of the supporting peelable flaps outside a sealing edge of a peeling side of the packaging; the supporting material comprises hard plastic, metal and paper, and corners of the supporting material are passivated.

2. The aseptic medical instrument packaging with supporting peelable flaps according to claim 1, wherein the hard plastic comprises phenolic plastic, polyurethane plastic, epoxy plastic, unsaturated polyester plastic, furan plastics, plastic made with organic silicon resin, plastic made with propenyl resin, or plastic made with modified resin.

3. The aseptic medical instrument packaging with supporting peelable flaps according to claim 1, wherein the metal comprises aluminum, steel, iron, platinum or alloy.

4. The aseptic medical instrument packaging with supporting peelable flaps according to claim 1, further comprising a groove carved in a junction between an outer edge of the sealing edge of the peeling side of the packaging and the extending part to facilitate peeling.

* * * * *